US00PP32538P2

(12) United States Plant Patent
Westervelt

(10) Patent No.: US PP32,538 P2
(45) Date of Patent: Dec. 1, 2020

(54) ***JUNIPERUS* TREE NAMED 'BUTTERFIELD'**

(50) Latin Name: *Juniperus virginiana*
Varietal Denomination: Butterfield

(71) Applicant: Keith D. Westervelt, Manhattan, KS (US)

(72) Inventor: Keith D. Westervelt, Manhattan, KS (US)

( * ) Notice: Subject to any disclaimer, the term of this patent is extended or adjusted under 35 U.S.C. 154(b) by 0 days.

(21) Appl. No.: 16/602,337

(22) Filed: Sep. 17, 2019

(51) Int. Cl.
*A01H 5/00* (2018.01)

(52) U.S. Cl.
USPC ..... Plt./214

(58) Field of Classification Search
USPC ..... Plt./214
CPC ..... A01H 5/00
See application file for complete search history.

*Primary Examiner* — Annette H Para
(74) *Attorney, Agent, or Firm* — Penny J. Aguirre

(57) ABSTRACT

A new cultivar of *Juniperus virginiana* plant named 'Butterfield' that is characterized by its soft, bright gold foliage in cold winter temperatures and in hot summer temperatures, it's very uniform growth habit and upright plant habit and its strong central leader.

1 Drawing Sheet

Botanical classification: *Juniperus virginiana.*
Varietal denomination: 'Butterfield'.

BACKGROUND OF THE INVENTION

The present invention relates to a new and distinct cultivar of *Juniperus* and will be referred to hereafter by its cultivar name, 'Butterfield'. 'Butterfield' is a new cultivar of juniper, an evergreen shrub grown for use as an ornamental landscape plant.

The inventor discovered 'Butterfield' as a chance seedling in January of 2014 that was growing in a field of unnamed and unpatented plants of *Juniperus virginiana* that was found in a residence yard in rural Lyon County, Kans.

Asexual propagation of the new cultivar was first accomplished by grafting onto *Juniperus* 'Hetzi' (not patented) understock in Manhattan, Kans. in January of 2014 under the direction of the Inventor. Asexual propagation by grafting has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Butterfield' as a unique cultivar of *Juniperus.*

1. 'Butterfield' exhibits soft, bright gold foliage in cold winter temperatures and in hot summer temperatures.
2. 'Butterfield' exhibits a very uniform growth habit and upright plant habit.
3. 'Butterfield' exhibits a strong central leader.

The plants that were present in the field that 'Butterfield' was discovered in were typical plants of the species *Juniperus virginiana* as there were no named cultivars amongst them. The plants all differed in lacking gold foliage in cold temperatures and in having non-uniform growth habits, and in lacking central leaders. 'Butterfield' can be compared to *Juniperus chinesis* cultivar 'Perfecta' (not patented) and

*Juniperus communis* cultivar 'Gold Cone' (not patented). 'Perfecta' and 'Gold Cone' are both similar to 'Butterfield' in having an upright habit. 'Perfecta' differs from 'Butterfield' in having foliage that is all green in color that is not as soft in texture and a growth habit that is less uniform in habit and shape. 'Gold Cone' differs from 'Butterfield' in having foliage that is not soft in texture and duller gold in color and in having a slower growth habit and a smaller plant size.

BRIEF DESCRIPTION OF THE DRAWING

The plant and plant parts depicted in the accompanied photograph illustrates the characteristics of 'Butterfield'. The photograph was taken of a four-year-old plant as grown outdoors in a 3-gallon container in Manhattan, Kans. FIG. 1 provides an overall view of the plant habit of 'Butterfield'. The colors in the photographs are as close as possible with the photographic and printing technology utilized. The color values cited in the detailed botanical description accurately describe the colors of the new *Juniperus.*

DETAILED BOTANICAL DESCRIPTION

The following is a detailed description of the new cultivar as taken from 2 year-old trees as grown outdoors in 1-gallon containers in Manhattan, Kans. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Evergreen shrub.

*Plant habit.*—Narrowly upright and uniform.

*Height and spread.*—An average of 39 cm in height and 18 cm in width, matures in the landscape to an average of 4.5 m in height and 3 m in spread.

*Cold hardiness.*—At least to U.S.D.A. Zone 6.

*Diseases and pests.*—No resistance and susceptibility to diseases or pests have been observed.

*Root description.*—Fibrous, moderately branched, moderately thick, primarily 199A in color.

*Growth rate.*—Moderate, 6 to 10 inches a year depending on moisture.

*Propagation.*—Grafting.

*Time to produce a young plant.*—6 to 8 weeks after grafting on 'Hetzi' understock.

Branch description:

*Branch shape.*—Rounded.

*Stem size.*—Main stem an average of 27 cm in length and 4 mm in diameter, trunk; an average of 6 mm in width at soil line, lateral stems an average of 11 cm in length and 3 mm in width.

*Branch surface.*—Surface covered with whorled, overlapping scale-like leaves, average of 5 mm in length and 3 mm in width, acute apex, cuneate base, surface when young; glabrous and matte, surface when maturing; slightly glossy and glabrous, surface when mature; dry and bark-like.

*Branching.*—Average of 34 lateral branches per main stem.

*Branch aspect.*—Held at an average angle of 80° (90°=vertical) to main stem.

*Internode length.*—Average of 3 mm.

*Branch color.*—Young; N144D, maturing; a blend of 174A and 161A, mature bark, 198A.

*Stem strength.*—Strong.

Foliage description:

*Leaf arrangement.*—Opposite and alternate.

*Leaf attachment.*—Sessile.

*Leaf shape.*—Lanceolate, scale-like.

*Leaf division.*—Simple.

*Leaf base.*—Cuneate.

*Leaf apex.*—Sharply pointed.

*Leaf venation.*—Not distinguishable.

*Leaf margins.*—Entire.

*Leaf fragrance.*—When crushed, the foliage produces a strong pleasant smell.

*Leaf surface.*—Young; upper and lower surfaces; glossy, glabrous, mature upper and lower surfaces; dull, glabrous.

*Leaf texture.*—Fine.

*Leaf color.*—Young upper and lower surface; 144A turning to 143A, mature upper and surface; and blend of 138A and NN137A.

*Leaf size.*—Linear needle; average of 6 mm in length and 1.8 mm in width, individual leaves an average of 1 mm in length and width, pointed apex, cuneate base, tightly overlapping.

*Leaf quantity.*—500 scale-like leaves per lateral branch.

Cone description: Cones have not observed on the new cultivar.

It is claimed:

1. A new and distinct cultivar of *Juniperus* plant named 'Butterfield' as herein illustrated and described.

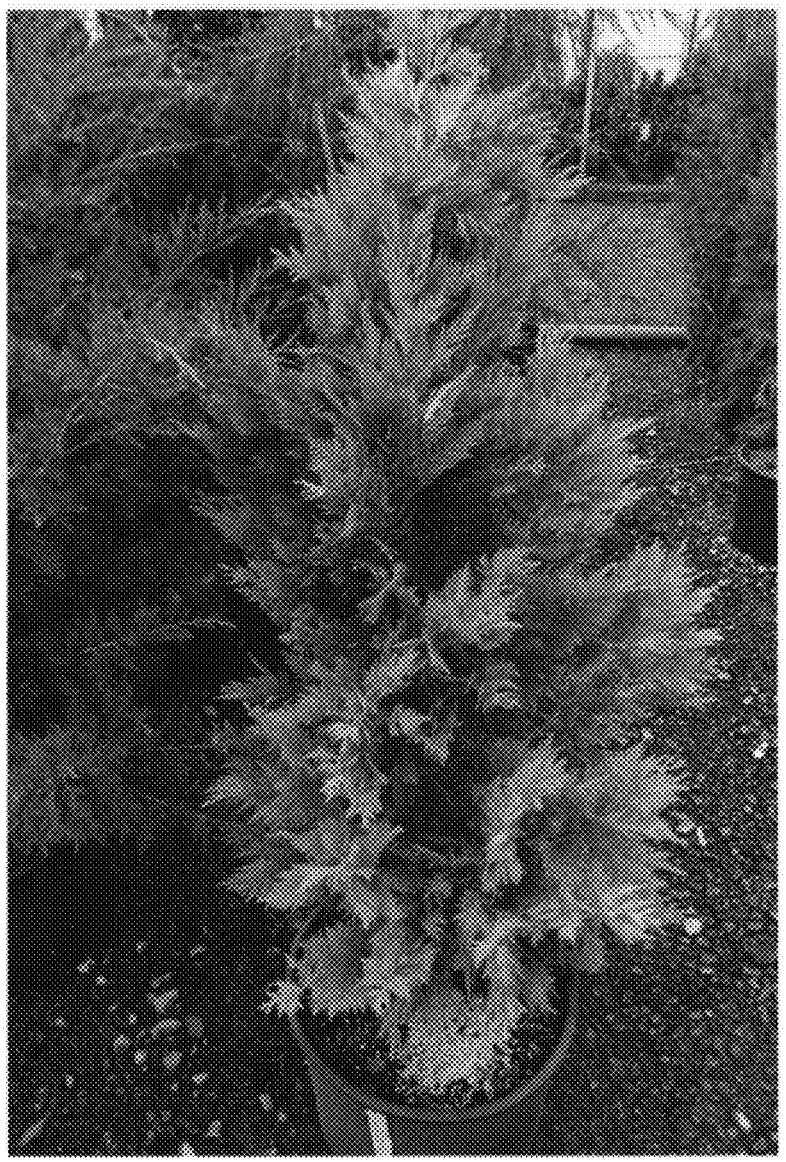

* * * * *